(12) United States Patent
Streff et al.

(10) Patent No.: US 9,039,415 B2
(45) Date of Patent: May 26, 2015

(54) CONNECTING SCREW FOR A DENTAL IMPLANT

(71) Applicant: Straumann Holding AG, Basel (CH)

(72) Inventors: Patrick Streff, Basel (CH); Edmund Suter, Basel (CH)

(73) Assignee: Straumann Holding AG, Basel (CH)

( * ) Notice: Subject to any disclaimer, the term of this patent is extended or adjusted under 35 U.S.C. 154(b) by 0 days.

(21) Appl. No.: 13/685,196

(22) Filed: Nov. 26, 2012

(65) Prior Publication Data

US 2013/0164708 A1 Jun. 27, 2013

(30) Foreign Application Priority Data

Dec. 22, 2011 (EP) .................................... 11010107

(51) Int. Cl.
*A61C 8/00* (2006.01)
*F16B 23/00* (2006.01)

(52) U.S. Cl.
CPC ............. *A61C 8/0048* (2013.01); *F16B 23/003* (2013.01); *A61C 8/0089* (2013.01)

(58) Field of Classification Search
CPC .................................................... A61C 8/0089
USPC .......... 433/173, 174; 411/402, 403, 410, 407, 411/409
See application file for complete search history.

(56) References Cited

U.S. PATENT DOCUMENTS

| 2,083,092 | A | * | 6/1937 | Richer ........................... 411/403 |
| 5,207,132 | A | * | 5/1993 | Goss et al. ...................... 81/460 |
| 6,419,489 | B1 | * | 7/2002 | Jorneus et al. ................ 433/141 |
| 6,663,388 | B1 | | 12/2003 | Schar |
| 2008/0233538 | A1 | * | 9/2008 | Hug et al. ...................... 433/174 |
| 2010/0167240 | A1 | * | 7/2010 | Benzon et al. ................. 433/174 |
| 2010/0297583 | A1 | | 11/2010 | Per Olof Leike |
| 2012/0103147 | A1 | * | 5/2012 | Farre Berga et al. ........... 81/460 |
| 2014/0186797 | A1 | * | 7/2014 | Haus ............................. 433/173 |

FOREIGN PATENT DOCUMENTS

| DE | 10 2004 026769 | 12/2004 |
| DE | 20 2008 003 187 | 5/2008 |
| EP | 1972297 | 9/2008 |
| WO | WO 00/38588 A1 | 7/2000 |
| WO | WO 2008/024062 A2 | 2/2008 |
| WO | WO 2008/116834 A1 | 10/2008 |

OTHER PUBLICATIONS

Jun. 22, 2012 EP Search Report and Written Opinion in corresponding EP 11 01 0107.

* cited by examiner

*Primary Examiner* — Ralph Lewis
(74) *Attorney, Agent, or Firm* — Novak Druce Connolly Bove + Quigg LLP (57) ABSTRACT

Connecting screw (22) for a dental implant (18) can be screwed securely by means of a commercially available rotary tool (24), even if the central longitudinal axis C of the connecting screw (22) and the longitudinal axis D of the rotary tool (24) are arranged at an acute angle to one another. For this purpose, the connecting screw (22) has a shaft portion (32) having an outer thread (48) for connection to the dental implant (18), and a head portion (34) having a blind-bore-shaped recess (36), which is open toward the upper screw end (46) and in which an engagement means (50) for the rotary tool (24) is formed integrally.

26 Claims, 5 Drawing Sheets

CONNECTING SCREW FOR A DENTAL IMPLANT

FIELD OF THE INVENTION

The present invention relates to a connecting screw for a dental implant.

BACKGROUND

Dental prostheses comprising a dental implant (also referred to as an anchoring part) inserted in the jaw and an abutment (also referred to as a body part or secondary part) fastened thereon are known sufficiently as a denture, wherein these two parts can also be formed as a unit (that is to say in one part and integrally). The abutment, which is preferably produced from metal or ceramics, wherein plastic or polymer compounds are also possible, is connected with a non-positive or positive fit to the dental implant by means of a screw. The screw is preferably produced from titanium, wherein embodiments made of steel are also possible however.

The prosthesis matched to the tooth profile is generally inserted as soon as the implant inserted in the patient's bone has healed, this insertion process being carried out by the treating doctor. A dental laboratory supplies the prosthesis components necessary for this, which are composed of the abutment with the tooth crown or bridge fabricated individually thereon and a (connecting) screw. To fix the abutment to the dental implant, the abutment is fitted on the implant; a connecting screw is then introduced through a bore in the abutment and is then screwed into an inner thread of the dental implant. The abutment and the dental implant are thus interconnected with a positive fit. The screw is generally tightened with a torque of more than 30 Nm, generally with a torque of approximately 35 Nm. Due to the confined spatial conditions in the mouth and as a result of the dimensions of the dental prosthesis, such connecting screws have to be relatively small so that they fit in the tooth crown.

A connecting screw within the meaning of the present invention can not only be used to fasten an abutment to a dental implant, but also to fasten a tooth crown to an abutment, a meso-abutment or a (one-part) dental implant.

A connecting screw of this type is known for example from DE 20 2008 003 187 U1. The connecting screw can also be formed in two parts, as disclosed in EP 1 972 297 A1 for example.

Such connecting screws typically have a shaft portion and a head portion. The shaft portion normally has a smaller diameter than the head portion and has an outer thread, which is screwed into the inner thread of the dental implant or abutment, whereas the head portion, when connected, rests on an inner shoulder in the bore in the abutment or the crown. In addition, an engagement means for a rotary tool is normally formed integrally on the head portion so that a sufficient torque can be transferred to the screw with the aid of a rotary tool.

This engagement means can be formed for example as an external or internal hexagon or as an external or internal torx, also referred to as a hexalobular external or internal driving feature. Standard EN DIN ISO 10664 describes a corresponding internal torx for screws and is hereby incorporated by reference.

The rotary tool comprises counter means corresponding to the engagement means of the screw. Rotary tools suitable for transferring a torque to a screw with an internal torx are likewise specified in standard EN DIN ISO 10664 for example and are hereby incorporated by reference.

An alternative embodiment of screw head and rotary tool is disclosed for example in DE 10 2004 026 769 A1.

One difficulty when anchoring the connecting screw in the dental implant is that a longitudinal axis of the bore in the abutment or the crown might not lie precisely in the extension of a longitudinal axis of the inner thread or of the dental implant, and instead these longitudinal axes are arranged at a certain angle to one another. A similar situation occurs if the bore inside the abutment or the tooth crown is angled. As a result of such an embodiment of the bore, the discharge opening of the bore may be placed in the tooth crown in such a way that it is not normally visible from the outside, that is to say the discharge opening can be arranged on the lingual or palatal side of the crown. However, it may also be necessary, due to the anatomical preconditions in a specific patient, for the bore to be angled or for the bore in the crown and the cavity in the implant to be arranged at an angle to one another.

In both cases, not only is it difficult to introduce the connecting screw through the bore in the abutment or crown into the inner thread of the dental implant, but it is also difficult in particular to tighten the screw with the aid of a rotary tool: such a rotary tool not only has to be brought into engagement through the bore with the engagement means on the connecting screw, but must also cooperate with said connecting screw in such a way that a torque sufficient to provide a reliable fastening can be transferred. To this end, the engagement means on the screw and the counter means on the rotary tool have to be matched to one another as precisely as possible so that the tool does not have too much play and the engagement means are not damaged.

The object of the present invention is therefore to allow a rotary tool to be introduced and a connecting screw to be tightened, even if the longitudinal axis of the bore in the abutment or the tooth crown and the longitudinal axis of the inner thread of the dental implant are arranged at an angle, in particular at an acute angle, to one another or if the bore is angled, that is to say if the rotary tool cannot be introduced into the screw in the extension of the central longitudinal axis thereof.

A similar object is achieved for example by WO 2008/024062 A2, in which a tooth crown has an angled cavity. A specific screwdriver having a flexible shaft is used to screw this tooth crown securely to an implant. This shaft may be formed for example by a plurality of interconnected wires or by a flexible core, for example made of plastic or polymer, surrounded by wires. This screwdriver disclosed in WO 2008/024062 A2 can bend in the region of the shaft and can thus adapt to the angled cavity in the tooth crown.

WO 2008/116834 A1 also discloses a specific screwdriver, which allows a screw to be tightened in an angled cavity. This screwdriver has a tip with a substantially rounded cross-section in the axial plane and a substantially polygonal cross-section in the radial plane. In addition, the polygon has at least two sides of different length so as to improve the transfer of a torque to a connecting screw, wherein the connecting screw must have a correspondingly shaped engagement depression, into which the screwdriver according to WO 2008/116834 A1 can be introduced.

In the prior art, the above-described object is thus achieved by using a specifically shaped screwdriver, wherein the screw may have to be adapted accordingly.

SUMMARY OF THE INVENTION

The present invention will provide a simpler solution, which likewise allows a torque to be transferred to a connecting screw for a dental implant when the longitudinal axis of the rotary tool does not coincide with the longitudinal axis of the connecting screw. In particular, the use of a commercially available rotary tool is to be made possible.

The connecting screw according to the invention for a dental implant comprises a shaft portion having a lower screw end and a head portion having an upper screw end located opposite the lower screw end, said portions being arranged along a central longitudinal axis C of the connecting screw. The shaft portion is typically substantially cylindrical or conical and has an outer thread for connection to the dental implant. The head portion is typically likewise substantially cylindrical or conical and has a blind-bore-shaped recess, which is open toward the upper screw end and in which an engagement means for a rotary tool is integrally formed. The rotary tool can be connected releasably to this engagement means such that a torque can be transferred from the rotary tool to the engagement means and therefore to the connecting screw.

The blind-bore-shaped recess expands radially below the engagement means toward the lower screw end and forms an undercut.

The engagement means has a plurality of engagement protrusions directed inwardly in the radial direction and distributed uniformly in the circumferential direction, each with an inner apex, and, centrally between each two adjacent engagement protrusions, has an engagement depression directed outwardly in the radial direction and with an outer apex in each case.

Each two diametrically opposed outer apices are arranged at a first distance A from one another and each two diametrically opposed inner apices are arranged at a second distance B from one another. The ratio A:B of the first distance A to the second distance B is preferably greater than 1.4.

At least one driving surface, which is defined by an upper end face falling radially inwardly in the direction of the lower screw end and by a lower undercut surface rising radially inwardly from the undercut to the upper screw end, extends over the engagement protrusions and engagement depressions. An upper borderline runs between the end face and the at least one driving surface, and a lower borderline runs between the undercut surface and the at least one driving surface.

The upper and the lower borderline are distanced from one another in the region of the outer apices of the engagement depressions by an outer distance $D_a$.

The connecting screw according to the invention is wherein the ratio $D_i:D_a$ of an inner distance $D_i$ between the upper borderline and the lower borderline in the region of the inner apices of the engagement protrusions to the outer distance $D_a$ is less than 0.5.

Due to the embodiment according to the invention of the engagement means, a rotary tool can even be introduced into the engagement means of the screw at an angle, that is to say when the longitudinal axis C of the connecting screw and the axis of rotation D of the rotary tool are arranged at an angle γ to one another. Reference is made to the descriptions of FIGS. 1a and 1b for a definition of this angle γ, these descriptions being provided further below and being applicable to the entire application.

This angle γ is typically an acute angle and may be up to 20°, preferably up to 30°. At the same time however, the transfer of a torque from the rotary tool to the connecting screw is in no way impaired. A sufficient torque can thus be transferred, whereby secure anchoring of the connecting screw is ensured. In particular, a torque of up to 35 Nm can be transferred without difficulty, without the connecting screw becoming damaged or otherwise impaired. Depending on the shape and type of implant, abutment, crown and screw, torques of approximately 15 to 35 Nm are typically transferred.

An important advantage of the connecting screw according to the invention lies in the fact that a commercially available rotary tool can be used to screw in the connecting screw. It is thus unnecessary to use a specifically designed or modified rotary tool.

The outer apices of the engagement depressions are apex lines, as is the case for example with a standard internal torx or standard internal hexagon. The apex lines run at least approximately parallel to the central longitudinal axis C of the connecting screw and are each the same height and are each arranged at the same distance from the central longitudinal axis C, as measured in the radial direction.

The upper and the lower borderline are arranged closer to one another in the region of the inner apices of the engagement protrusions. The inner distance $D_i$ in the region of the inner apices is thus smaller than the outer distance $D_a$ in the region of the outer apices, and the two borderlines advance toward one another from the outer apices toward the inner apices.

Since the blind-bore-shaped recess expands below the engagement means and forms an undercut, the tip of the rotary tool can protrude further outwards in the lower region of the recess, that is to say further away from the central longitudinal axis C of the connecting screw. Together with the above-specified ratio $D_i:D_a$, this allows the longitudinal axis D of the rotary tool to be angled with respect to the longitudinal axis C of the connecting screw, without impairing the transfer of torque in the process. In particular, the rotary tool and connecting screw still have a sufficiently large contact area, which is arranged substantially radially.

In a preferred embodiment, the ratio $D_i:D_a$ is less than 0.3, preferably less than 0.2 and more preferably less than 0.1. The ratio $D_i:D_a$ is thus essentially smaller if the inner distance $D_i$ is smaller, that is to say if the upper and lower borderline are arranged closer to one another in the region of the inner apices. By advancing the upper and lower borderline toward one another in the region of the inner apices, that is to say by reducing the inner distance $D_i$, the angle γ at which the rotary tool can still be introduced into the engagement means and transfer the desired torque is greater.

In accordance with a preferred embodiment, the upper and lower borderline at least approximately contact one another, but preferably do not actually contact one another, in the region of the inner apices of the engagement protrusions. This means that the upper and the lower borderline, which run substantially in the circumferential direction, advance increasingly toward one another when they approach an inner apex in the circumferential direction, and preferably contact one another, that is to say coincide, at the apex, and in so doing form a vertex. The engagement protrusions thus have a pyramid-tip-shaped contour. The inner apices of the engagement protrusions are therefore at least approximately pointed; the points preferably being vertices. These vertices all lie in a plane lying perpendicular to the central longitudinal axis C of the connecting screw and all have the same distance from the central longitudinal axis C of the screw, as measured in this plane. All vertices thus lie over a circle, which lies in a plane lying perpendicular to the longitudinal axis of the connecting screw, and of which the midpoint lies over the central longitudinal axis C of the connecting screw.

Alternatively, it is also possible for the upper and lower borderline to just approximately contact one another in the region of the inner apices, that is to say for the ratio $D_i:D_a$ to indeed be small, but >0. In this case too, the distance between the two borderlines decreases increasingly if said borderlines approach the inner apex in the circumferential direction; the upper and the lower borderline never actually contact one another however.

The inner distance $D_i$ between the upper and the lower borderline is preferably less than 0.1 mm, and more preferably less than 0.05 mm.

The outer distance $D_a$ is typically between 0.3 mm and 0.8 mm, preferably between 0.3 mm and 0.6 mm, and in particular is 0.4 mm.

In accordance with a preferred embodiment, a connecting line between the upper and the lower borderline is curved, that is to say rounded, at the inner apex toward the central longitudinal axis C of the connecting screw. This simplifies the introduction of the rotary tool at an angle. The curvature of the borderline may be equal throughout, so that the borderline forms part of a circle, or the curvature may increase or decrease in the direction of the lower borderline, wherein it preferably decreases. The radius of such a curved connecting line may be approximately 0.1 mm for example.

In a preferred embodiment, the ratio A:B is greater than 1.4, in particular greater than 1.45, but is preferably no greater than 1.55, and is more preferably approximately 1.5. In this case too, a greater ratio of A:B tends to enable a greater angle γ, provided the contact area between the rotary tool and the engagement means of the screw is also sufficiently large.

The first distance A is preferably 1.8 mm to 2.0 mm, and in particular is 1.9 mm.

The second distance B is preferably 1.2 mm to 1.4 mm, and in particular is 1.3 mm.

The engagement means of the connecting screw according to the invention preferably has between 3 and 8 of each of the engagement protrusions and the engagement depressions.

In a preferred embodiment, the engagement means has six engagement protrusions and six engagement depressions, which are preferably rounded in the circumferential direction. The screw according to the invention therefore particularly preferably has an engagement means in the form of a modified internal torx, also referred to as a hexalobular internal driving feature. It is important that the screw according to the invention can be screwed in using a corresponding commercially available rotary tool. In this regard, reference is made to the above-mentioned standard EN DIN ISO 10664. With six engagement protrusions and six engagement depressions, the angular distance between each two adjacent outer apices is 60°, and therefore the outer apices form an equilateral hexagon. The same also applies to the angular distance between two adjacent inner apices, wherein the inner apices likewise form an equilateral hexagon.

In a preferred embodiment the blind-bore-shaped recess additionally has an inner thread. Such an inner thread can be used for connection to an abutment or another prosthesis element. The inner thread is preferably arranged below the engagement means and the undercut, that is to say closer to the lower screw end.

In a preferred embodiment the blind-bore-shaped recess additionally has an internal hexagon, in particular an internal hexagon according to standard EN DIN ISO 10664, which is arranged below the above-described engagement means. With such a connecting screw, a rotary tool can be connected releasably to the connecting screw, both at an angle γ and in the extension of the central longitudinal axis C of said connecting screw, so that a torque can be transferred. Should the rotary tool be introduced in a straight line, that is to say in the extension of the central longitudinal axis C, it connects to the lower internal hexagon; if, by contrast, the rotary tool is introduced at an angle γ, it thus cooperates with the upper engagement means. The connecting screw according to the invention can thus be used in a versatile manner.

In a preferred embodiment, the shaft portion has an outer diameter of 1.0 mm to 2.2 mm, and in particular of 1.6 mm.

In a preferred embodiment, the head portion has an outer diameter of 1.5 mm to 3.5 mm, and in particular of 2.5 mm.

In a preferred embodiment, the shaft portion is 5.0 mm to 10.0 mm tall, and in particular is 7.0 mm tall.

In a preferred embodiment, the head portion is 0.8 mm to 1.6 mm tall, and in particular is 1.2 mm tall.

The above dimensions for the diameter and height of the screw parts correspond to those of connecting screws that are currently used typically in known dental implant systems. Depending on the application of the connecting screw, it would also be possible of course to select the outer diameters and heights so as to be greater or smaller.

In a preferred embodiment, the connecting screw consists of metal or ceramics, in particular of titanium, a titanium alloy, stainless steel or zirconium oxide. These materials are particularly well suited, since they demonstrate sufficient stability for application in the field of dental implants and can also be brought into the desired shape without difficulty. In addition, connecting screws made of these materials can be easily cleaned and sterilized, which is vital for application in implantology in order to prevent infections and other undesirable side effects.

The connecting screw according to the invention is preferably formed in one part. This facilitates cleaning and sterilization of the screw.

In a preferred embodiment, a surface normal of the undercut surface encloses an angle α of 20° to 60°, preferably of 30° to 50°, with the longitudinal axis C of the connecting screw. Reference is made to the descriptions of FIGS. 4 and 5 for a definition of this angle α, these descriptions being provided further below and being applicable to the entire application. The introduction of the rotary tool into the connecting screw is facilitated as a result of such a relatively steep embodiment of the undercut surface.

In a preferred embodiment, a commercially available torx screwdriver can be introduced into the engagement means of the connecting screw according to the invention, even if the longitudinal axis of the screw and that of the screwdriver are arranged at an acute angle to one another. In particular, the screwdriver can be introduced into the engagement means at an angle γ of up to 15°, preferably at an angle γ of up to 20°, preferably up to 30°, with respect to the longitudinal axis C of the screw. This allows trouble-free introduction, even in difficult cases.

In a preferred embodiment, the head portion has an at least substantially circular cylindrical outer shape, of which the outer diameter is greater than that of the shaft portion, an annular shoulder surface running between the head portion. As a result of this embodiment, the screw can only be introduced into the dental implant up to a predetermined depth, specifically until the shoulder surface rests against a corresponding counter surface of the abutment, and the implant and abutment can be securely interconnected.

It is particularly preferable if a surface normal of the annular shoulder surface encloses an β of 0° to 45°, in particular of approximately 30°, with the longitudinal axis C of the connecting screw. Reference is made to the descriptions of FIGS. 4 and 5 for a definition of this angle β, these descriptions being provided further below and being applicable to the entire application.

The connecting screw according to the invention can be purchased individually or as part of a set containing further similar connecting screws and/or a suitable rotary tool. Alternatively, it would also be possible to combine the connecting screw with a dental implant and/or abutment. In addition, the number of individual components within this set can of course be varied as desired.

BRIEF DESCRIPTION OF THE DRAWINGS

Three preferred embodiments of the connecting screw according to the invention will be described in greater detail on the basis of the following drawings, in which, purely schematically:

FIG. 1b shows an enlargement of the screw head and rotary tool from FIG. 1a;

FIG. 3a shows a perspective illustration of a commercially available rotary tool;

FIG. 3b shows an enlargement of the tip of the rotary tool from FIG. 3a;

FIGS. 9 a-d each show a section through the head portion of a connecting screw according to the invention, which is connected to a rotary tool.

DETAILED DESCRIPTION

Figure 1A:
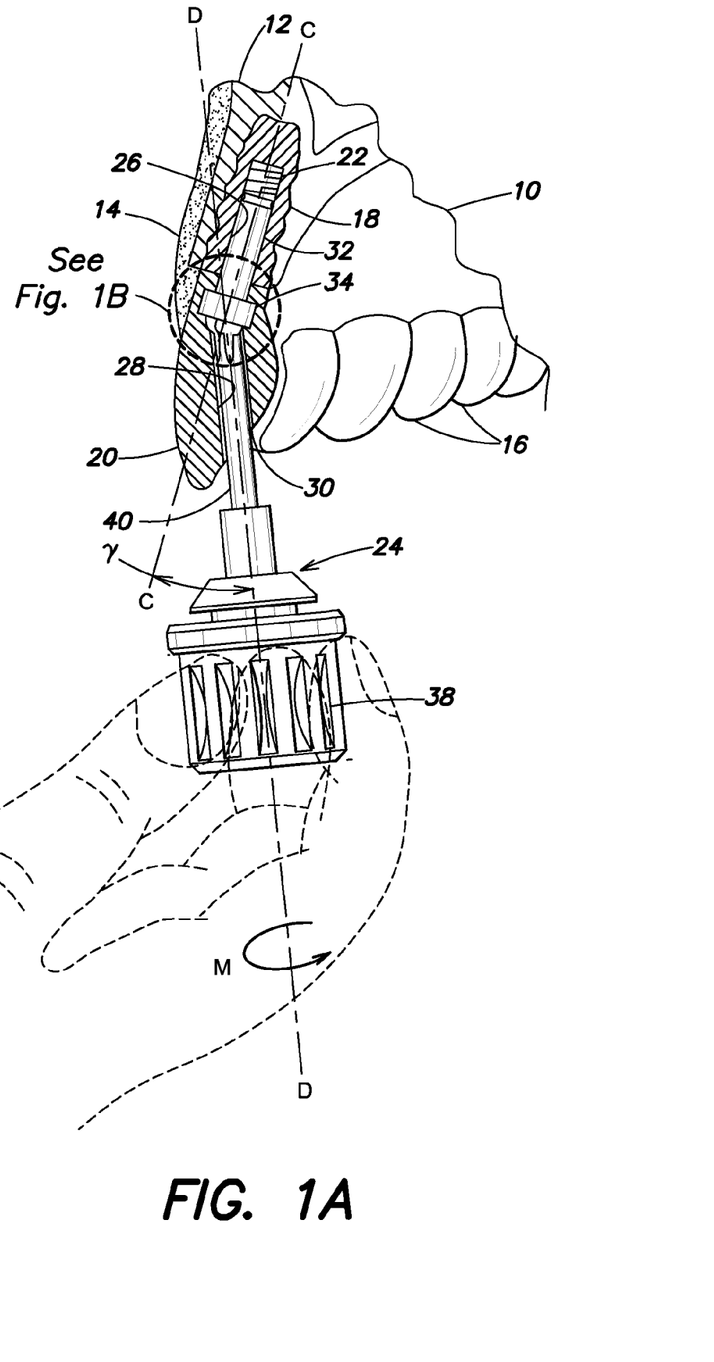
FIG. 1a shows the screwing in of a connecting screw according to the invention by means of a commercially available rotary tool.

FIG. 1a shows a portion of a patient's upper jaw 10 with a jaw bone 12, a soft tissue 14 surrounding the jaw bone 12, a plurality of remaining, natural teeth 16, and an artificial denture, consisting of a dental implant 18 and a tooth crown 20. The tooth crown 20 is connected to the dental implant 18 by means of a connecting screw 22 according to the invention. To this end, a torque M is transferred to the connecting screw 22 with the aid of a commercially available rotary tool 24, and said connecting screw is thus screwed into the dental implant 18. The subsequent descriptions of course also apply analogously to a lower jaw.

The dental implant 18 shown is a one-part "bone-level implant", which is sunk practically completely in the patient's jaw bone 12. The dental implant 18 is substantially circular cylindrical, consists typically of metal, for example titanium or a titanium alloy, or ceramics, for example zirconium dioxide, and has an outer thread for anchoring in the jaw bone 12. In addition, the dental implant 18 has a substantially circular cylindrical cavity 26 with an inner thread, which runs parallel to a central longitudinal axis of the dental implant 18 and into which the connecting screw 22 can be screwed. The alignment or inclination of the dental implant 18, and therefore also of the central longitudinal axis, is determined substantially by the jaw bone 22 and the position of the surrounding natural (or artificial) teeth 16.

The tooth crown 20, which typically consists of ceramics, protrudes from the soft tissue 14 into the patient's oral cavity. Alternatively, it would also be possible to connect the dental implant 18 to an abutment (not shown), on which the tooth crown 20 is fitted in turn. The tooth crown 20 has a continuous cylindrical bore 28 having a discharge opening 30, through which the connecting screw 22 can be introduced. The discharge opening 30 is arranged on the inner side of the tooth crown 20, that is to say the lingual or palatal side, so that it is not visible from outside the oral cavity.

In the case of the denture shown in FIG. 1a, the cavity 26 in the dental implant 18 and the bore 28 in the tooth crown 20 are arranged at an acute angle γ to one another. This means that a central longitudinal axis D of the rotary tool 24 likewise has to be inclined by the angle γ with respect to the central longitudinal axis of the dental implant 18 whilst the rotary tool 24 is introduced into, or engaged with, the connecting screw 22 for the transfer of the torque M. This angle γ may be up to 20°, preferably up to 30°.

The connecting screw 22 according to the invention comprises a shaft portion 32 and a head portion 34. The shaft portion 32 has an outer thread for connection to the dental implant 18. The head portion 213 has a blind-bore-shaped recess 36, into which the rotary tool 24 can be introduced for releasable connection to the connecting screw 22. The connecting screw 22 is introduced into the cavity 26 in the dental implant 18 in such a way that its central longitudinal axis C coincides with the central longitudinal axis of the dental implant.

The rotary tool 24 shown in FIG. 1a is a commercially available screwdriver comprising an external torx. The rotary tool 24 comprises a grip part 38, which can be held by a user's fingers, and a working part 40 connected thereto and comprising a tip 42. The tip 42 is used to temporarily engage in the connecting screw 22 and to transfer a torque M thereto. To this end, the tip 42 is introduced into the blind-bore-shaped recess 36 in the connecting screw 22.

Figure 1B:
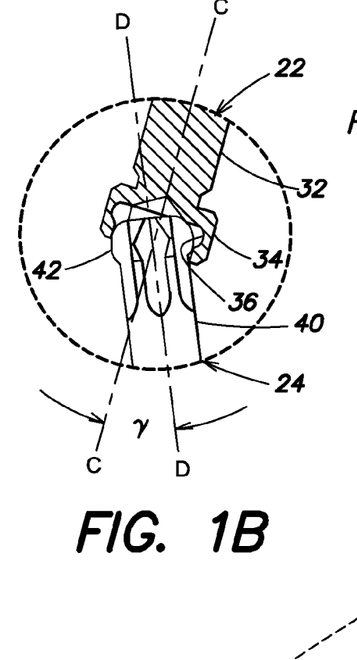

FIG. 1b shows an enlarged detail from FIG. 1a, in which the releasable connection between the connecting screw 22 and the rotary tool 24 is illustrated. In this case too, it can clearly be seen that the central longitudinal axis of the dental implant 18 and the connecting screw 22 is inclined by an acute angle γ with respect to the central longitudinal axis D of the rotary tool. Due to the embodiment according to the invention of the connecting screw 22, it is ensured that the torque M is transferred without difficulty in spite of this inclination.

Figure 2:
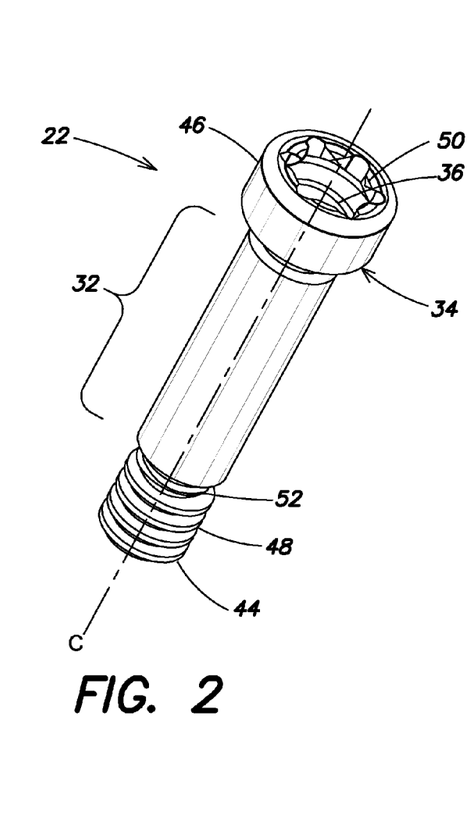
FIG. 2 shows a perspective illustration of a first preferred embodiment of a connecting screw according to the invention.

FIG. 2 shows a perspective illustration of a first preferred embodiment of the connecting screw 22 according to the invention. This screw comprises a shaft portion 32 with a lower screw end 44 and a head portion 34 with an upper screw end 46, and preferably consists of metal or ceramics, in particular of titanium, a titanium alloy, stainless steel or zirconium oxide. It is particularly preferable if the connecting screw 22 is formed in one part. The shaft portion 32 has an outer thread 48 for connection to the dental implant 18 (not shown here). The head portion 34 comprises a blind-bore-shaped recess 36, which is open toward the upper screw end 46 and in which an engagement means 50 for the rotary tool 24 (not shown here) is formed integrally.

In the case of the connecting screw 22 shown in FIG. 2, both the shaft portion 32 and the head portion 34 are substantially circular cylindrical. The shaft portion 32 is narrower, but much taller, than the head portion 34. The shaft portion 32 has a circumferential groove 52 above the outer thread 48.

Figures 3A, 3B:
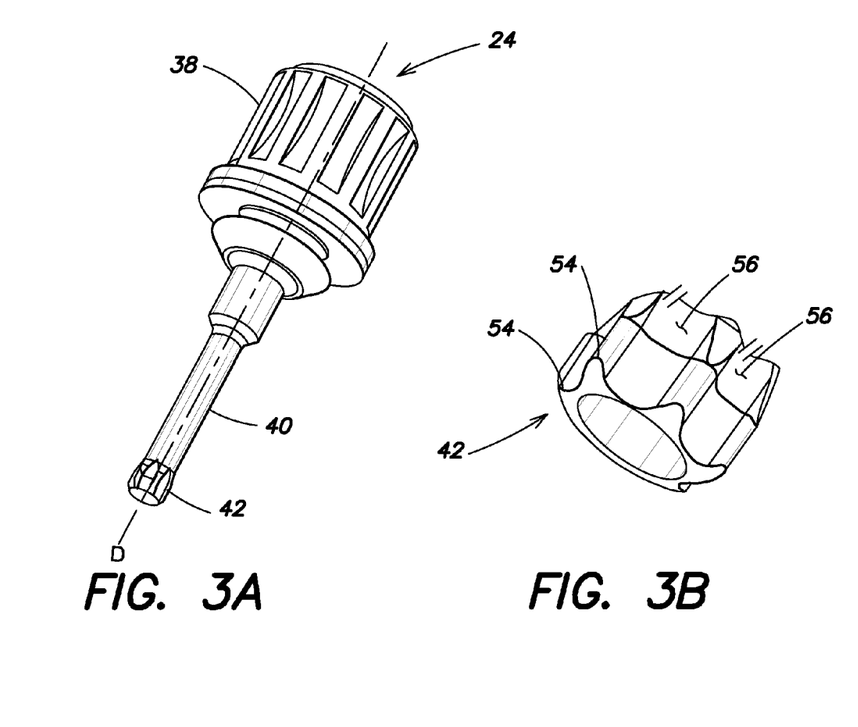

FIGS. 3a and 3b show a commercially available rotary tool 24, as is currently used typically to screw a connecting screw 22 (not shown here) into a dental implant 18 (not shown here). This rotary tool 24 comprises a grip part 38 and a working part 40 connected thereto and comprising a tip 42. The tip 42, which is illustrated in FIG. 3b in an enlarged manner is used to temporarily engage in the connecting screw 22 and to transfer a torque thereto. To this end, the tip 42 shown has six protrusions 54, which are distributed uniformly in the circumferential direction, are directed radially outwardly and are rounded in the circumferential direction, and has a radially inwardly directed depression 56, likewise rounded in the circumferential direction, arranged between each of said protrusions. These protrusions 54 and depressions 56 are intended to cooperate with the engagement means 50 of the connecting screw 22 (not shown here). The rotary tool 24 shown in FIGS. 3a and 3b thus has an external torx or hexalobular external driving feature. Alternatively, depending on the embodiment of the engagement means 50 of the connecting screw 22, it would also be possible to use a different commercially available rotary tool matched to said engagement means of the connecting screw.

Figures 4, 5, 6:
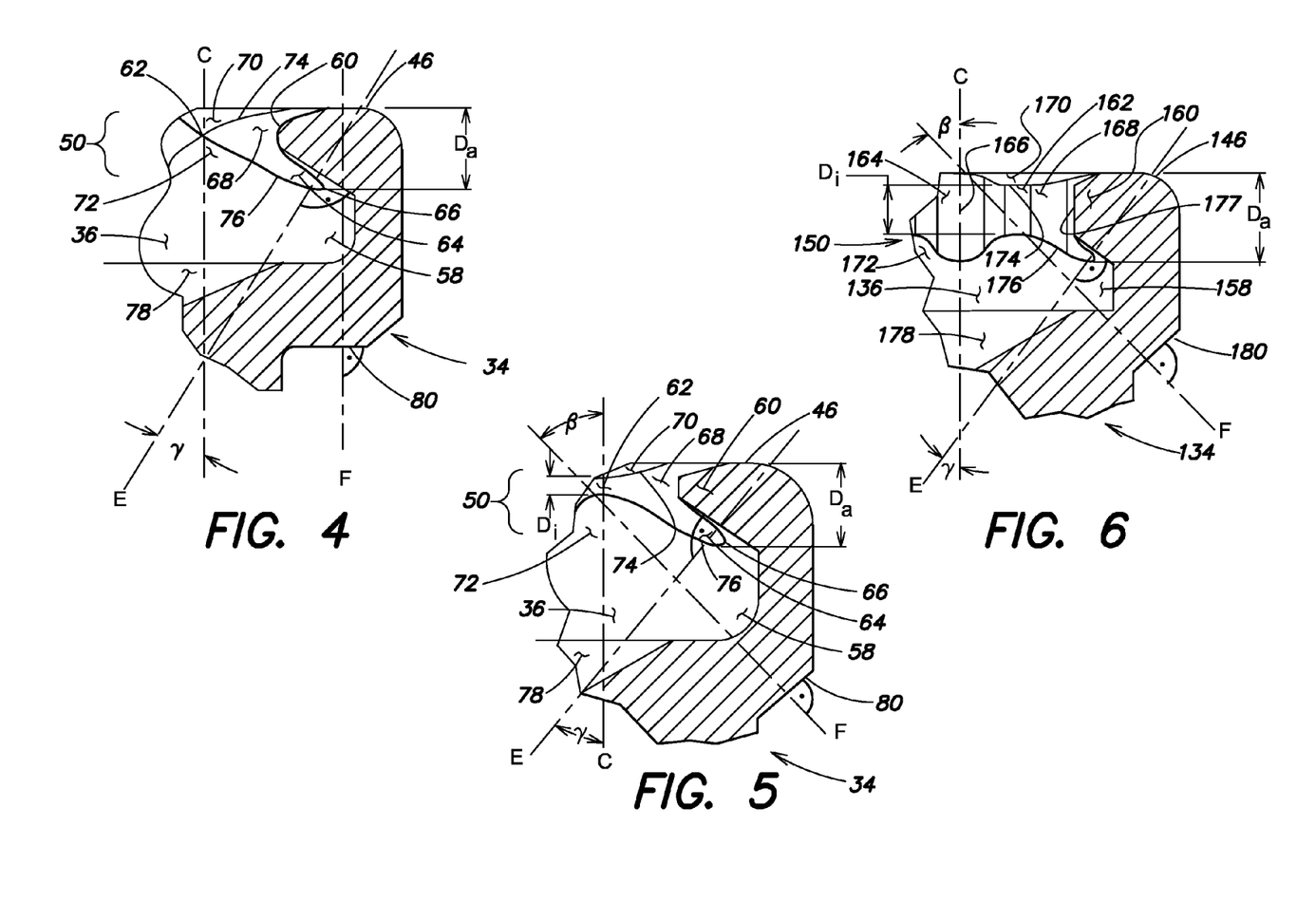
FIG. 4 shows a section through the head portion of the first preferred embodiment of a connecting screw according to the invention.
FIG. 5 shows a section through the head portion of a second preferred embodiment of a connecting screw according to the invention.
FIG. 6 shows a section through the head portion of a connecting screw with a standard internal torx according to the prior art.

FIGS. 4 and 5 each show a section through the head portion 34 of a connecting screw 22 according to the invention, whereas FIG. 6 shows a section through the head portion 134 of a screw having a standard internal torx. To differentiate, the components with the standard internal torx are each provided hereinafter with a reference sign in the 100s, whereas the numbering used above will be continued in the case of the connecting screw 22 according to the invention.

All three head portions 34, 134 have a blind-bore-shaped recess 36, 136, which is open toward the upper screw end 46, 146 and comprises an engagement means 50, 150 formed integrally therein for a rotary tool. The blind-bore-shaped recess 36, 136 expands below the engagement means 50, 150 and forms an undercut 58, 158.

The engagement means 50, 150 each comprise a plurality of (in each of the illustrated cases six) rounded engagement protrusions 60, 160 directed inwardly in the radial direction. Each of these engagement protrusions 60, 160 has an inner apex 62, 162. In the case of a standard internal torx according to FIG. 6 and in the embodiment according to FIG. 5, this inner apex 62, 162 is designed as an apex line or apex surface, whereas the inner apex 60 in the embodiment according to FIG. 4 is point-like or at least approximately point-like. A rounded engagement depression 64, 164, which is directed outwardly in the radial direction and has an outer apex 66, 166 in each case is located in the circumferential direction between each of the engagement protrusions 60, 160. The outer apices 66, 166 are formed as apex lines in all three cases.

A further difference lies in the fact that, in the case of a standard internal torx and in the embodiment according to FIG. 5, an individual continuous driving surface 68, 168 running substantially parallel to the longitudinal axis C of the screw in the circumferential direction extends over the engagement protrusions 60, 160 and engagement depressions 64, 164, whereas the driving surface 68 in the embodiment shown according to FIG. 4 is divided into a plurality of (in the illustrated case six) separate portions, which contact one another at the inner vertices 62. In the embodiment according to the invention according to FIG. 5 however, the driving surface 68 narrows much more severely in the region of the inner apex 62 than is the case with the driving surface 168 of the commercially available screw according to FIG. 6.

The driving surfaces 68, 168 are defined in the axial direction on one side by an upper, radially inwardly falling end face 70, 170 and on the other side by a lower undercut surface 72, 172 rising radially inwardly from the undercut 58, 158. An upper borderline 74, 174 runs between the end face 70, 170 and the at least one driving surface 68, 168, and a lower borderline 76, 176 runs between the undercut surface 72, 172 and the at least one driving surface 68, 168.

In the case of a standard internal torx according to FIG. 6 and in the embodiment according to FIG. 5, the upper borderline 74, 174 and the lower borderline 76, 176 are distanced from one another over the entire circumference. By contrast, in the particularly preferred embodiment according to FIG. 4, the upper borderline 74 and the lower borderline 174 are distanced from one another in the region of the outer apices 66, whereas they contact one another in the region of the inner apices 62. In the embodiment according to FIG. 4, the upper borderline 74 and the lower borderline 76 thus each form a vertex on the engagement protrusions 60. At each of these points, the end face 70, the undercut surface 72 and each two adjacent parts of the driving surface 68 contact one another and form a pyramid-tip-shaped protrusion directed toward the central longitudinal axis of the connecting screw 22.

In each of FIGS. 5 and 6, a connecting line 77, 177 can be seen over the surface of the engagement means 50, 150 between the upper borderline 74, 174 and the lower borderline 76, 176 and, in both cases, has the form of a straight line. By contrast, in a preferred embodiment not shown in the figures, this connecting line 77 is curved, that is to say rounded, between the upper borderline 74 and the lower borderline 76 at the inner apex 62 toward the central longitudinal axis C of the connecting screw 22.

In the region of the outer apices 66, 166, the upper borderline 74, 174 and the lower borderline 76, 176 are distanced from one another by an outer distance $D_a$. In the region of the inner apices 62, 162, the upper borderline 74, 174 and the lower borderline 76, 176 are distanced from one another by an inner distance $D_i$, wherein, in the case of the connecting screw according to the invention, $D_i$ may also be 0 (shown in FIG. 4).

In the two embodiments according to the invention according to FIGS. 4 and 5, the ratio $D_i:D_a$ is 0.5 at most. By contrast, in the case of the screw from the prior art shown in FIG. 6, the ratio $D_i:D_a$ is much greater.

As a result of this embodiment of the connecting screw according to the invention, the commercially available rotary tool 24 from FIGS. 3a and 3b is connected releasably to the engagement means 50 and can be used to transfer a torque, even when the longitudinal axis C of the connecting screw 22 is arranged at an acute angle γ to the longitudinal axis D of the rotary tool 24. The tip 42 of the rotary tool 24 is thus introduced into the blind-bore-shaped recess 36 in the head portion 34 of the connecting screw 22 and cooperates with the engagement means 50. In doing so, the protrusions 54 on the rotary tool 24 engage in the engagement depressions 64 in the connecting screw 22, whilst the engagement protrusions 60 of the connecting screw 22 engage in the depressions 56 in the rotary tool 24. An efficient transfer of torque from the rotary tool 24 to the connecting screw 22 is thus possible.

This operative connection between the tip 42 of the rotary tool 24 and the engagement means 50 of the connecting screw 22 according to the invention is thus possible even if, as shown in FIGS. 1a and 1b, the longitudinal axis D of the rotary tool 24 is arranged at an acute angle γ of up to 20°, preferably up to 30°, relative to the longitudinal axis C of the connecting screw 22. In addition, thanks to the specific embodiment of the engagement means 50, the connecting screw 22 according to the invention allows introduction and removal of the tip 42 of the rotary tool 24 into and from the engagement means 50, even with an acute angle of up to 20°, preferably up to 30°, between the two longitudinal axes D, C of the rotary tool 24 and connecting screw 22.

The blind-bore-shaped recess expands below the engagement means 50, 150 to form an undercut 58, 158. This undercut is substantially circular cylindrical in all three cases and is defined upwardly by the undercut surface 72, 172. As mentioned above, the undercut surface 72, 172 rises inwardly from the undercut 58, 158, and is thus inclined with respect to the longitudinal axis C of the connecting screw 22. A surface normal E relative to the undercut surface 72, 172 encloses an angle α from 20° to 60°, preferably from 30° to 50°, with the longitudinal axis C.

A conically tapering transition region 78, 178, which ultimately transitions into a fastening region (not visible) for fastening of an abutment or a tooth crown, in turn adjoins the undercut 58, 158 in the direction of the lower screw end (not visible here).

The head portion 34, 134 in the screws shown in FIGS. 4, 5 and 6 has a substantially circular cylindrical outer shape. The outer diameter of the head portion 34, 134 is greater than that of the adjacent shaft portion 32, 132, wherein an annular shoulder surface 80, 180 runs between the head portion 34, 134 and the shaft portion 32, 132.

In the embodiment shown in FIG. 4, a surface normal F relative to the annular shoulder surface 80 is arranged substantially parallel to the longitudinal axis C of the connecting screw 22, and thus encloses an angle β of 0° therewith. In the embodiment shown in FIG. 5, the surface normal F relative to the annular shoulder surface 80 encloses an acute angle β of approximately 30° with the longitudinal axis C of the connecting screw 22.

In addition to the shoulder surfaces 80 shown in FIGS. 4 and 5, all combinations of a plurality of shoulder surfaces having identical or different inclination, which enable a transition from the broader head portion 34 to the narrower shaft portion 32, are also conceivable however. The shoulder surface 80 is intended, when assembled, to rest against a corresponding counter surface in the abutment or the crown (not shown) and to thus stabilize the connection and simultaneously prevent the connecting screw 22 from being introduced too deeply.

Figure 7:
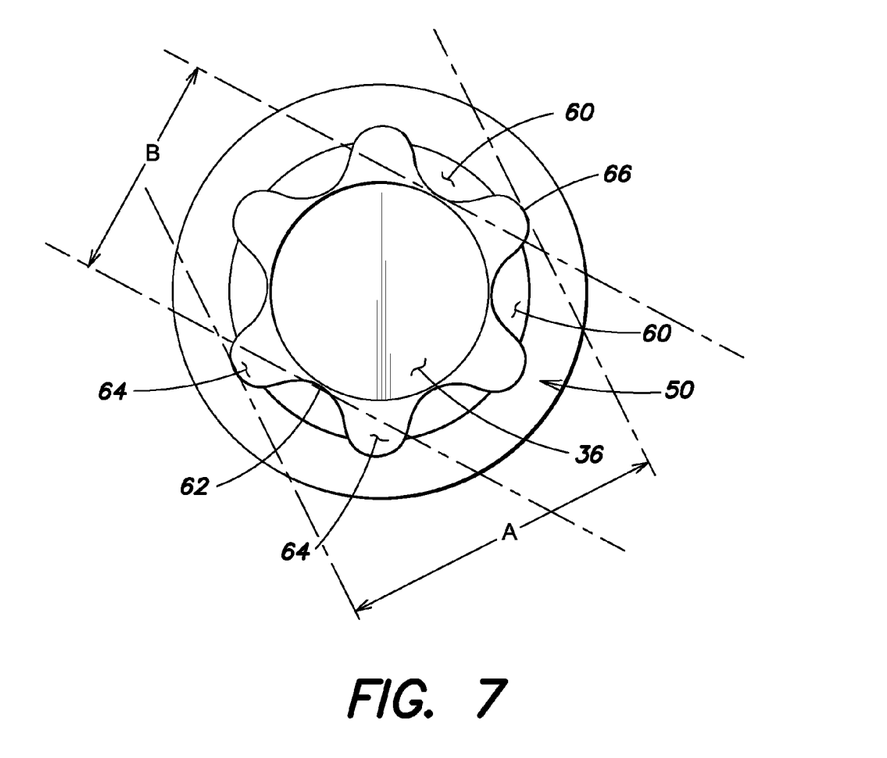
FIG. 7 shows a plan view of the upper end of the connecting screw from FIG. 4.

FIG. 7 shows a plan view of the connecting screw 22 from FIG. 4. The engagement means 50 formed integrally in the blind-bore-shaped recess 36 has six rounded engagement protrusions 60 directed inwardly in the radial direction and distributed uniformly in the circumferential direction, each having an inner apex 62, and has a rounded engagement depression 64, with an outer apex 66, directed outwardly in the radial direction and located centrally between each of said engagement protrusions. The distance between two diametrically opposed outer apices 66 is denoted by A, whereas the distance between each two diametrically opposed inner apices 62 is denoted as B. The ratio A:B is preferably at least 1.4 in the case of the connecting screw 22 according to the invention.

Figure 8:
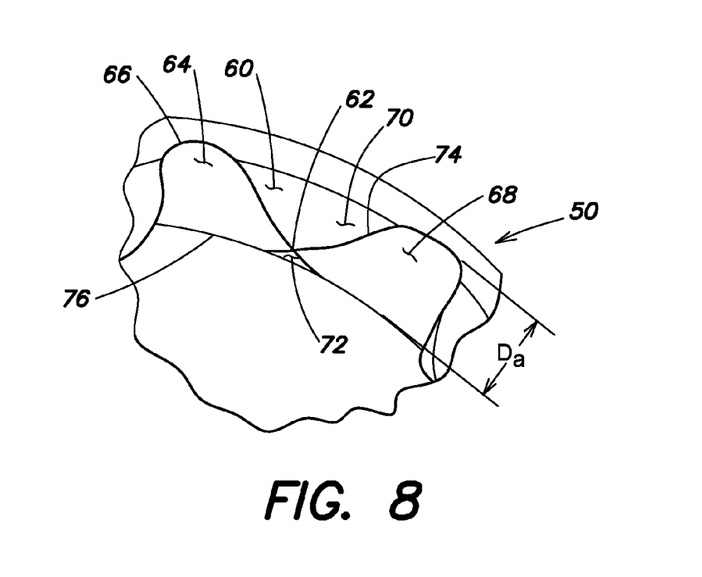
FIG. 8 shows an enlargement of the engagement means of the connecting screw from FIG. 4.

FIG. 8 shows an enlarged, perspective illustration of a detail of the engagement means 50 in the blind-bore-shaped recess 36 in the connecting screw 22 according to the invention according to FIG. 4. Some of the engagement protrusions 60, each having an inner apex 62, and some of the engagement depressions 64, each having an outer apex 66, can be seen in this case. The engagement surfaces 68, which are separated upwardly by the upper borderline 74 from the end face 70 and downwardly by the lower borderline 76 from the undercut surface 72, extend over said engagement protrusions and depressions. In the region of the outer apices 66, the upper borderline 74 and the lower borderline 76 extend approximately parallel to one another and are distanced from one another by the outer distance $D_a$, whereas they advance increasingly closer toward the inner apices 62 and ultimately contact one another at the apex 62.

Figure 9A:
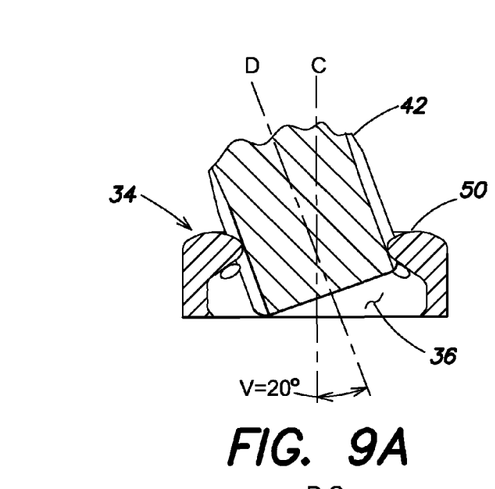
Figure 9B:
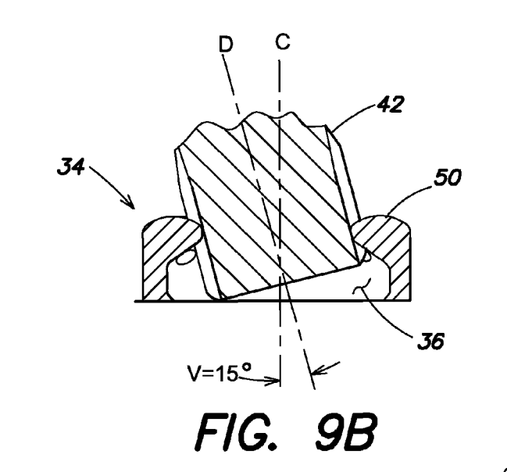
Figure 9C:
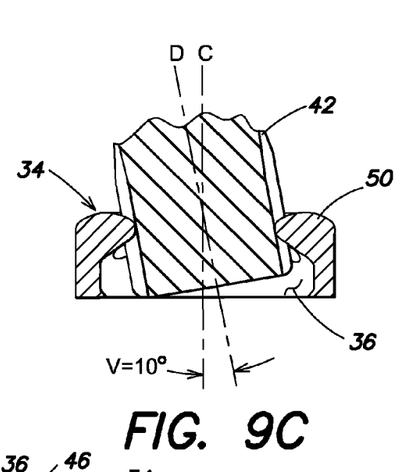
Figure 9D:
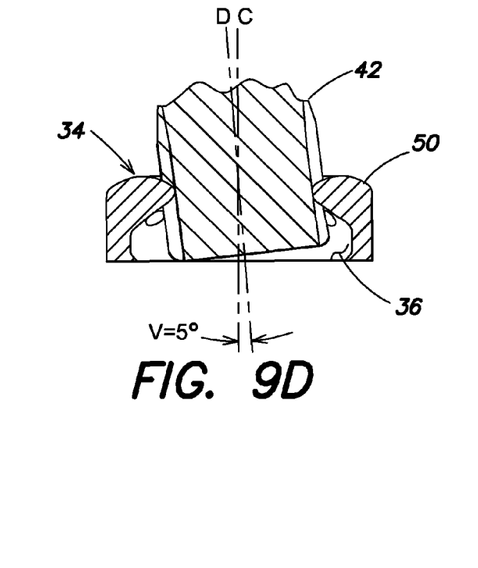

FIGS. 9a to 9d each show a section through the upper part of the head portion 34 of a connecting screw 22 according to the invention, wherein, in each case, a tip 42 of a commercially available rotary tool 24 is introduced into the blind-bore-shaped depression 36, where it cooperates with the engagement means 50. FIGS. 9a to 9d each differ in terms of the angle γ between the central longitudinal axis C of the connecting screw 22 and the longitudinal axis D of the rotary tool 24, that is to say the rotary tool 24 is, in each case, introduced into the connecting screw 22 at a different acute angle γ. FIG. 9a shows an angle γ of 20°, FIG. 9b shows an angle γ of 15°, FIG. 9c shows an angle γ of 10°, and FIG. 9d shows an angle γ of 5°. In all four cases, a releasable, yet rotationally secure, connection is formed between the engagement means 50 and the tip 42 for the transfer of a torque M from the rotary tool 24 to the connecting screw 22.

Figure 10:
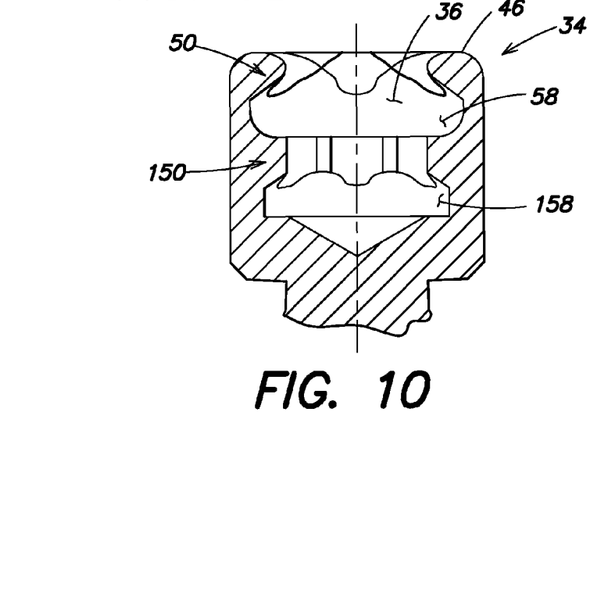
FIG. 10 shows a section through the head portion of a third preferred embodiment of a connecting screw according to the invention.

FIG. 10 shows a section through the head portion 34 of a third preferred embodiment of a connecting screw according to the invention. The head portion 34 likewise has a blind-bore-shaped recess 36, which is open toward the upper screw end 46. In the upper region facing toward the upper screw end 46, a first engagement means 50 is formed integrally in the blind-bore-shaped recess 36 and corresponds to that in the embodiment shown in FIG. 4. Alternatively, it would also be possible for the first engagement means 50 to correspond to that in the embodiment shown in FIG. 5, wherein the connecting line 77 can be a straight line (as shown in FIG. 5) or a curve curved toward the central longitudinal axis C. Below the engagement means 50, the blind-bore-shaped recess 36 expands to form a first undercut 58.

In addition, a second engagement means 150 in the form of an internal hexagon, in particular an internal hexagon according to standard EN DIN ISO 10664, is formed integrally in the lower region, facing toward the lower screw end 44 (not visible), of the blind-bore-shaped recess 36. A similar engagement means 150 is also illustrated in FIG. 6 and is described in detail with reference to said figure. The blind-bore-shaped recess 36 likewise expands below the second engagement means 150 and forms a second undercut 158.

As a result of this embodiment, a rotary tool 24 can be introduced either in the extension of the central longitudinal axis C of the connecting screw 22 and connected releasably thereto, wherein the rotary tool 24 cooperates with the second engagement means 150 to transfer a torque M, or can be introduced at an angle γ, wherein the rotary tool 24 cooperates with the first engagement means 50.

The invention claimed is:

1. A connecting screw for a dental implant, comprising a shaft portion having a lower screw end and a head portion having an upper screw end located opposite the lower screw end, said portions being arranged along a central longitudinal axis C of the connecting screw, the shaft portion having an outer thread for connection to the dental implant and the head portion having a blind-bore-shaped recess, which is open toward the upper screw end and in which an engagement means for a rotary tool is integrally formed, the blind-bore-shaped recess expanding radially below the engagement means toward the lower screw end and forming an undercut, the engagement means having a plurality of engagement protrusions directed inwardly in the radial direction and distributed uniformly in the circumferential direction, each with an inner apex, and, centrally between each two adjacent engagement protrusions, having an engagement depression directed outwardly in the radial direction and with an outer apex in each case, each two diametrically opposed outer apices being arranged at a first distance A from one another and each two diametrically opposed inner apices being arranged at a second distance B from one another, at least one driving surface, which is defined by an upper end face falling radially inwardly in the direction of the lower screw end and by a lower undercut surface rising radially inwardly from the undercut to the upper screw end, extending over the engagement protrusions and engagement depressions, and an upper borderline running between the end face and the at least one driving surface, and a lower borderline running between the undercut surface and the at least one driving surface, and the upper borderline and the lower borderline being distanced from one another in the region of the outer apices of the engagement depressions by an outer distance $D_a$, wherein the ratio $D_i:D_a$ of an inner distance $D_i$ between the upper borderline and the lower borderline in the region of the inner apices of the engagement protrusions to the outer distance $D_a$ is less than 0.5.

2. The connecting screw as claimed in claim 1, wherein the ratio $D_i:D_a$ is less than 0.3.

3. The connecting screw as claimed in claim 1, wherein the lower borderline and the upper borderline contact one another in the region of the inner apices of the engagement protrusions.

4. The connecting screw as claimed in claim 1, wherein the inner distance $D_i$ is less than 0.1 mm.

5. The connecting screw as claimed in claim 1, wherein the outer distance $D_a$ is between 0.3 mm and 0.8 mm.

6. The connecting screw as claimed in claim 1, wherein a connecting line between the upper borderline and the lower borderline is curved at the inner apex toward the central longitudinal axis C of the connecting screw.

7. The connecting screw as claimed in claim 1, wherein the ratio A:B is greater than 1.

8. The connecting screw as claimed in claim 1, wherein the first distance A is 1.8 mm to 2.0 mm.

9. The connecting screw as claimed in claim 1, wherein the second distance B is 1.2 mm to 1.4 mm.

10. The connecting screw as claimed in claim 1, wherein the engagement means has six engagement protrusions and six engagement depressions.

11. The connecting screw as claimed in claim 1, wherein the blind-bore-shaped recess additionally has an internal hexagon which is arranged below the engagement means.

12. The connecting screw as claimed in claim 1, wherein the connecting screw consists of metal or ceramics.

13. The connecting screw as claimed in claim 1, wherein the connecting screw is formed in one part.

14. The connecting screw as claimed in claim 1, wherein a surface normal E of the undercut surface encloses an angle $\alpha$ of 20° to 60° with the longitudinal axis C of the connecting screw.

15. The connecting screw as claimed in claim 1, wherein a torx screwdriver can be introduced into the engagement means at an angle $\gamma$ of up to 20° with respect to the longitudinal axis C of the connecting screw.

16. The connecting screw as claimed in claim 1, wherein the head portion has a substantially circular cylindrical outer shape, of which the outer diameter is greater than that of the shaft portion, an annular shoulder surface running between the head portion and the shaft portion and a surface normal F of the annular shoulder surface (80) enclosing an angle $\beta$ with the longitudinal axis C of the connecting screw.

17. The connecting screw as claimed in claim 1, wherein the ratio $D_i:D_a$ is less than 0.2.

18. The connecting screw as claimed in claim 1, wherein the ratio $D_i:D_a$ is less than 0.1.

19. The connecting screw as claimed in claim 18, wherein $D_i$ is less than 0.1 mm and $D_a$ is between 0.3 mm and 0.8 mm.

20. The connecting screw as claimed in claim 1, wherein the connecting screw comprises titanium, a titanium alloy, stainless steel or zirconium oxide.

21. The connecting screw as claimed in claim 1, wherein the inner distance $D_i$ is less than 0.05 mm.

22. The connecting screw as claimed in claim 1, wherein the ratio A:B is greater than 1.45.

23. The connecting screw as claimed in claim 1, wherein the head portion has a substantially circular cylindrical outer shape, of which the outer diameter is greater than that of the shaft portion, an annular shoulder surface running between the head portion and the shaft portion and a surface normal F of the annular shoulder surface (80) enclosing an angle 13 of 0° to 45° with the longitudinal axis C of the connecting screw.

24. The connecting screw as claimed in claim 1, wherein a torx screwdriver in accordance with standard EN DIN ISO 10664 can be introduced into the engagement means at an angle $\gamma$ of up to 20° with respect to the longitudinal axis C of the connecting screw.

25. A connecting screw for a dental implant, comprising a shaft portion having a lower screw end and a head portion having an upper screw end located opposite the lower screw end, said portions being arranged along a central longitudinal axis C of the connecting screw, the shaft portion having an outer thread for connection to the dental implant and the head portion having a blind-bore-shaped recess, which is open toward the upper screw end and in which an engagement means for a rotary tool is integrally formed, the blind-bore-shaped recess expanding radially below the engagement means toward the lower screw end and forming an undercut, the engagement means having a plurality of engagement protrusions directed inwardly in the radial direction and distributed uniformly in the circumferential direction, each with an inner apex, and, centrally between each two adjacent engagement protrusions, having an engagement depression directed outwardly in the radial direction and with an outer apex in each case, each two diametrically opposed outer apices being arranged at a first distance A from one another and each two diametrically opposed inner apices being arranged at a second distance B from one another, at least one driving surface, which is defined by an upper end face falling radially inwardly in the direction of the lower screw end and by a lower undercut surface rising radially inwardly from the undercut to the upper screw end, extending over the engagement protrusions and engagement depressions, and an upper borderline running between the end face and the at least one driving surface, and a lower borderline running between the undercut surface and the at least one driving surface, the upper borderline and the lower borderline being distanced from one another in the region of the outer apices of the engagement depressions by an outer distance $D_a$, wherein the ratio $D_i:D_a$ of an inner distance $D_i$ between the upper borderline and the lower borderline in the region of the inner apices of the engagement protrusions to the outer distance $D_a$ is less than 0.5; and wherein the lower borderline and the upper borderline contact one another in the region of the inner apices of the engagement protrusions.

26. An abutment and connecting screw for connecting the abutment to a dental implant, comprising:

the abutment having a bore configured to receive the connecting screw for attaching the abutment to a dental implant, wherein the bore of the abutment is disposed at an acute angle with respect to a longitudinal axis of a bore of the dental implant for receiving the connecting screw; and the connecting screw comprising:

a shaft portion having a lower screw end and a head portion having an upper screw end located opposite the lower screw end, said portions being arranged along a central longitudinal axis C of the connecting screw, the shaft portion having an outer thread for connection to the dental implant and the head portion having a blind-bore-shaped recess, which is open toward the upper screw end and in which an engagement means for a rotary tool is integrally formed, the blind-bore-shaped recess expanding radially below the engagement means toward the lower screw end and forming an undercut, the engagement means having a plurality of engagement protrusions directed inwardly in the radial direction and distributed uniformly in the circumferential direction, each with an inner apex, and, centrally between each two adjacent engagement protrusions, having an engagement depression directed outwardly in the radial direction and with an outer apex in each case, each two diametrically opposed outer apices being arranged at a first distance A from one another and each two diametrically opposed inner apices being arranged at a second distance B from one another, at least one driving surface, which is defined by an upper end face falling radially inwardly in the direction of the lower screw end and by a lower undercut surface rising radially inwardly from the undercut to the upper screw end, extending over the engagement protrusions and engagement depressions, and an upper borderline running between the end face and the at least one driving surface, and a lower borderline running between the undercut surface and the at least one driving surface, and the upper borderline and the lower borderline being distanced from one another in the region of the outer apices of the engagement depressions by an outer distance Da, wherein the ratio Di:Da of an inner distance Di between the upper borderline and the lower borderline in the region of the inner apices of the engagement protrusions to the outer distance Da is less than 0.5.

* * * * *

UNITED STATES PATENT AND TRADEMARK OFFICE
CERTIFICATE OF CORRECTION

| | | |
|---|---|---|
| PATENT NO. | : 9,039,415 B2 | Page 1 of 1 |
| APPLICATION NO. | : 13/685196 | |
| DATED | : May 26, 2015 | |
| INVENTOR(S) | : Streff et al. | |

It is certified that error appears in the above-identified patent and that said Letters Patent is hereby corrected as shown below:

In the Claims

In claim 23, line 24 delete "13" and insert --B--.

Signed and Sealed this
Twenty-ninth Day of September, 2015

Michelle K. Lee
*Director of the United States Patent and Trademark Office*